United States Patent [19]

Nitzan

[11] Patent Number: 4,802,489
[45] Date of Patent: Feb. 7, 1989

[54] METHOD FOR CARRYING OUT BLOOD FLOW MEASUREMENTS AND A PROBE THEREFOR

[75] Inventor: Meir Nitzan, Mizrach Binyamin, Israel

[73] Assignee: Jerusalem College of Technology, Jerusalem, Israel

[21] Appl. No.: 76,785

[22] Filed: Jul. 23, 1987

[30] Foreign Application Priority Data

Jul. 29, 1986 [IL] Israel ............................... 79541

[51] Int. Cl.⁴ .............................................. A61B 5/02
[52] U.S. Cl. ................................... 128/691; 128/736
[58] Field of Search .................. 128/688, 691, 736; 374/179, 208–210

[56] References Cited

U.S. PATENT DOCUMENTS

| | | | |
|---|---|---|---|
| Re. 30,317 | 7/1980 | Lubbers et al. | 128/691 X |
| 3,626,757 | 12/1971 | Benzinger | 128/736 |
| 4,308,870 | 1/1982 | Arkans | 128/736 X |
| 4,354,504 | 10/1982 | Bro | 128/736 X |
| 4,487,208 | 12/1984 | Kamens | 128/736 |
| 4,494,550 | 1/1985 | Blazek et al. | 128/691 X |
| 4,595,020 | 6/1986 | Palti | 128/736 |
| 4,677,985 | 7/1987 | Bro et al. | 128/691 |

Primary Examiner—Kyle L. Howell
Assistant Examiner—Angela D. Sykes
Attorney, Agent, or Firm—Amster, Rothstein & Ebenstein

[57] ABSTRACT

A probe for regional blood flow measurement, comprising a housing of low thermal conduction and heat capacity, at least one face of which is adapted to make contact with a tissue region investigated, the face being provided with a recessed portion, a relatively thin plate made of a material of high thermal conductivity, located in the recess and being substantially flush with the tissue-contacting face of the housing, a temperature-sensing means in thermal contact with the plate and adapted to transfer temperature-related information to the outside of the housing, wherein the respective configurations of the plate and the housing are such as to minimize the area of contact between them relative to the area of contact between the plate and the tissue region, in order to minimize heat flow between the plate and the housing. A method for carrying out regional blood flow measurements is also disclosed.

12 Claims, 4 Drawing Sheets

METHOD FOR CARRYING OUT BLOOD FLOW MEASUREMENTS AND A PROBE THEREFOR

BACKGROUND OF THE INVENTION

The present invention relates to a method for regional blood flow measurement. It further relates to a probe for making such measurements.

Assessment of regional blood flow (RBF) of various organs, i.e., of the volume of blood perfusing a unit volume of tissue per unit of time, has both clinical and physiological significance. Many methods, optical, thermal, acoustical, electrical, radioactive and other were developed for RBF measurements but their clinical application is still limited. Most of the methods provide only qualitative results, while transient clearance methods, which can assess RBF quantitatively with no need for in-vivo calibration, are, in general, hazardous. In transient clearance methods some dilutant is administered to the investigated tissue, either by inhalation or by injection, and RBF is derived from the dependence of the dilutant concentration on time. The commonly used dilutant is either 133Xe or H2. Both materials are hazardous when administered by inhalation, while their injection into the investigated tissue interferes with blood flow.

The relative convenience of thermal measurement has motivated several attempts to evaluate RBF by thermal methods, using the wellknown function of the blood: transferring deep-body heat to the environment. Direct measurement of the temperature of uncovered tissue provides some information on tissue blood flow, which is one of the factors determining tissue temperature. However, this information is only qualitative, since tissue temperature depends also on many other parameters such as tissue conductivity, evaporation rate, radiation and air convection. Direct temperature measurements are valuable only for qualitative comparison of adjacent tissue surfaces, as is done in thermography.

Heat clearance measurements are more directly related to blood flow itself. Many steady-state heat clearance methods—invasive and non-invasive, constant-power or isothermal—have been developed in the last fifty years, with various degrees of success. Analysis of the steady-state methods reveals however, that the amount of heat dissipation by blood flow depends also on the probe geometry as well as on tissue conductivity, necessitating in-vivo calibration in order to obtain quantitative results.

Recently, preliminary results were disclosed of a transient thermal clearance method, in which the dilutant is (negative) heat. A metal plate, thermally insulated from its surroundings, is attached to the investigated tissue, and its temperature is measured by means of a copper-constantan thermocouple embedded in it. The plate temperature is increased towards an equilibrium temperature which, under conditions of perfect thermal insulation, equals the local arterial blood temperature. The rate of heat transfer to the tissue surface depends both on tissue thermal conduction and on heat convection by blood. However, after enough time has elapsed and temperature gradients have been decreased, the main contribution to heat transfer is due to heat convection by blood. At this tage, surface temperature (and the metal plate temperature) is an exponential function of time. Plotting $\Delta T$, the difference between instantanous plate temperature and equilibrium temperature as a function of time on a semi-logarithmic scale, provides a straight line from whose slope, the time constant $\tau$ of the $\Delta T$-against-time curve, can be derived. The aimed-for regional blood flow F is merely the reciprocal of $\tau$. Because of the high values of the time constant (generally 100–600 secons) the final equilibrium temperature $T_b$ is achieved only after 5-25 minutes. When an organ with pathologic blood flow is examined, measurement time may be even longer. The main drawback of the known transient thermal clearance method is its long measurement time. Besides the inconvenience accompanying clinical measurements of long duration, the possible changes in regional blood flow during the long time of measurement interferes with the measurement and reduces its accuracy. Since fluctuations in skin blood flow are a common phenomenon, a severe limitation to the potential applications of the method is inevitable.

The long measurement time of the known transient thermal clearance method is mainly due to the need for determining $T_b$, the final equilibrium temperature. Since the known method is based on calculating the slope of the curve of $\Delta T(=T-T_b)$ against time, it is necessary to obtain the equilibrium temperature $T_b$. As was noted earlier, this requires much time, especially with low regional blood flow.

Measurement time is further increased due to the fact that the rate of temperature increase at the beginning of measurement does not provide quantitative information about blood flow. This is because heat transfer during this period is substantially influenced by tissue heat conduction. According to the known thermal clearance method, application of (negative) heat is effected by the attachment of a metal plate at room temperature, which results in appreciable temperature gradients in the tissue and high contribution of thermal conduction to heat transfer. Thus, the unproductive first phase of measurement is prolonged, and more time has to elapse until one may assume that a condition of small temperature gradients has been obtained. A solution to the problem may be a probe with means to cool its metal plate and the tissue underneath continuously when attached to the skin. Moderate cooling for long periods of time will result in thermal gradients which for the same average reduction of tissue temperature, are smaller than those obtained by abrupt cooling at lower temperatures. In previous experiments, continuous moderate cooling was effected by water flowing through a polyethylene tube, which was attached to the metal plate. Although results showed an appreciable reduction in the first phase of conductive temperature increase, the heat capacity of the tube and the remaining water interfered with the results.

While the main disadvantage of the known method resided in the need, explained above, to continue the test until the equilibrium temperature $T_b$ has been established, the known probe, which consisted of a metal disk mounted along its entire periphery in a teflon housing, aggravated and added to, this disadvantage in that it undermined the basic assumption of the transient thermal clearance method, according to which all the heat transfered by the blood goes towards heating the tissue and the metal plate. As it turned out, the known probe leaks heat from the metal plate to the housing in two ways: by heat conduction from the relatively large peripheral area of contact with the housing, and by radiation, through the air gap between them, from the back of the plate to the housing walls, the material of which, teflon, was found to be less of an efficient thermal insulation than was originally assumed. These heat losses, besides interfering with the measurement (especially when organs of low regional blood flow are investigated), also prolong measurement time, since more time has to elapse until the metal plate reaches its equilibrium temperature. Moreover, heat leakage is higher during the beginning of the measurement (when thermal gradients between the metal plate and the capsule are higher), thereby increasing deviation of the $\Delta T$ vs. time curve from the exponential. Thus, the appropriate instant for blood flow measurements is further delayed.

It is one of the objects of the present invention to overcome the above-mentioned difficulties and drawbacks of the prior-art methods for regional blood-flow measurements, and to propose a method that is inherently safe, gives accurate results even with low regional blood flows, and does not require the attainment of equilibrium temperature $T_b$.

SUMMARY OF THE INVENTION

This the present invention achieves by providing a method for carrying out regional blood flow measurements, comprising the steps of:

providing a probe attachable to the tissue region to be investigated and adapted to produce a signal indicative of the surface temperature of said tissue region;

arbitrarily establishing at least two equal periods of time, a first and a second period;

substracting the temperature at the beginning of said first period from the temperature at the end of said first period, obtaining a first difference;

subtracting the temperature at the beginning of said second period from the temperature at the end of said second period, obtaining a second difference;

integrating the temperature over said second period, to obtain a first integral;

integrating the temperature over said first period, to obtain a second integral;

determining said flow by subtracting said second difference from said first difference, and dividing the result by the difference between said first integral and said second integral.

It is a further object of the present invention to improve upon the prior-art probes by largely eliminating undesirable heat flow.

This the present invention achieves by providing a probe for regional blood flow measurement, comprising:

a housing of low thermal conduction and heat capacity, at least one face of which is adapted to make contact with a tissue region investigated, said face being provided with a recessed portion;

a relatively thin plate made of a material of high thermal conductivity, located in said recess and being substantially flush with said tissue-contacting face of said housing;

a temperature-sensing means in thermal contact with said plate and adapted to transfer temperature-related information to the outside of said housing, wherein the respective configurations of said plate and said housing are such as to minimize the area of contact between them relative to the area of contact between said plate and said tissue region, in order to minimize heat flow between said plate and said housing.

BRIEF DESCRIPTION OF THE DRAWING

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 represents a typical temperature-vs.-time curve as plotted with the aid of the probe according to the invention;

FIG. 2 is a view, in cross section along planes II—II in FIG. 3, of a preferred embodiment of the probe.

FIG. 3 is a bottom view of the probe of FIG. 2;

FIG. 4 is a partial, greatly enlarged view of the tissue-contacting face of the plate;

FIG. 5 is a partial cross section of the plate, showing its engagement with one of the mounting rods;

FIGS. 6 and 7 illustrate two other methods of holding the plate inside the housing recess;

FIG. 8 represents an air-coolable plate;

FIG. 9 is a block diagram showing the general set up, including two air-cooled probes, and FIG. 10 is a block diagram of the analyzer.

DETAILED DESCRIPTION OF THE PREFERRED EMBODIMENTS

Figure 1:
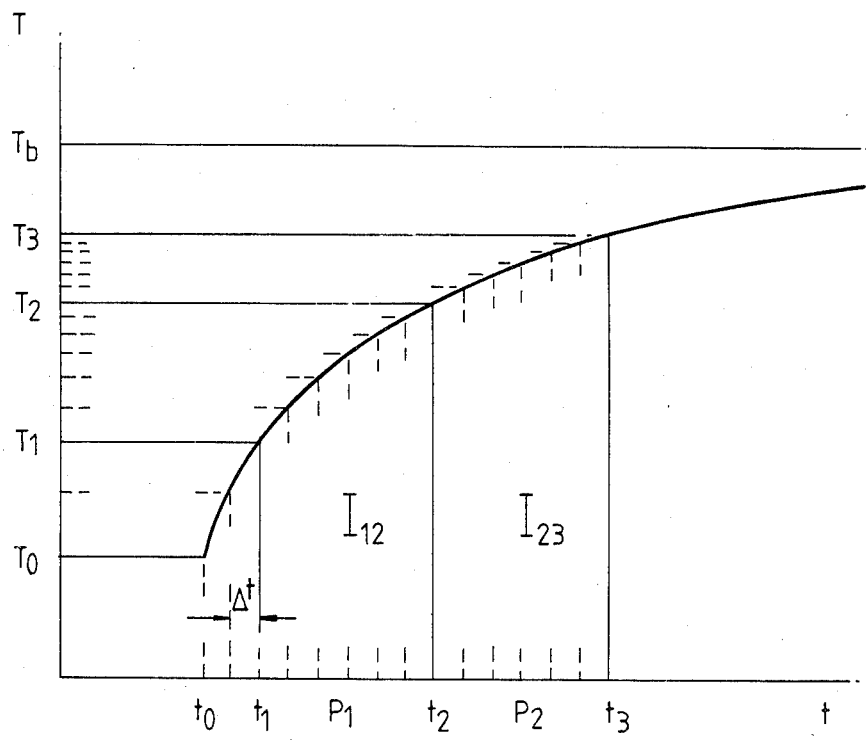

Referring now to the drawings, there is seen in FIG. 1 a typical temperature-vs.-time curve as plotted with the aid of the probe. The procedure is basically very simple: by selecting three temperatures $T_1$, $T_2$, $T_3$, taken at times $t_1$, $t_2$ and $t_3$ respectively, the flow F can be determined, without the need to wait until equilibrium temperature $T_b$ has been attained. While the time periods $P_1=(t_2-t_1)$ and $P_2=(t_3-t_2)$ must be equal, they need not be contiguous as shown in FIG. 1. They may overlap to some extent, or there may be a gap between $P_1$ and $P_2$. The expression used to calculate the regional blood flow is:

$$F = \frac{(T_2 - T_1) - (T_3 - T_2)}{I_{23} - I_{12}}$$

Actually, in order to eliminate random instantaneous temperature fluctuations, it is good practise to use the average value of T in the range $(t_i-t, t_i+t)$, instead of the instantaneous $T_i$.

The areas $I_{23}$ and $I_{12}$ represent the integrals of the temperature over periods $P_2$ and $P_1$, respectively.

Some precautions are in order when choosing the values of $t_1$, $t_2$ and $t_3$. $t_1$ must be taken a long enough time after $t_o$, the initiation of measurement, in order to avoid appreciable thermal conduction effects. On the other hand, inreasing the value of $t_1-t_o$ reduces the value of $T_2-T_1$, (for the same value of $t_2-t_1$). A similar compromise has to be reached for the choice of the value of $t_2-t_1$. Too small a value of $t_2-t_1$ results in a small value of $T_2-T_1$ with high relative fluctuations, while too high a value of it increases measurement time. It should be noted that the appropriate choice of $t_1-t_o$ and $t_2-t_1$ depends on the order of magnitude of the blood flow. Thus, when designing a data analyzer, it is advantageous to have freedom in determining the values of $t_1$, $t_2$ and $t_3$.

A preferred embodiment of the probe according to the invention is illustrated in FIGS. 2 to 5.

Figure 2:
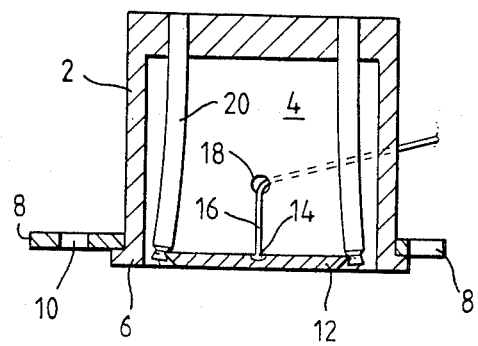
Figure 3:
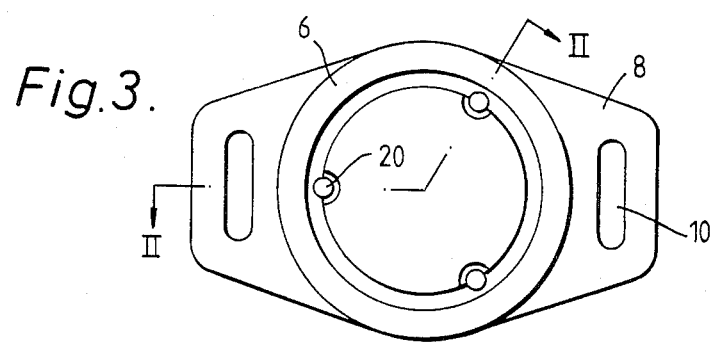

There is seen in FIG. 2 a substantially cylindrical housing 2, closed at one end, and recessed at the outer end, to form a space 4 the recessed end is provided with a flange 6 adapted to make contact with the tissue to be investigated. The housing 2 must obviously be made of a material of low thermal conductivity and heat capacity, and have smooth, easily cleanable and cold-sterilizable surfaces. A material that was found particularly suitble is structural foam, which is easily moldable as well as machinable. Also, its molded surfaces tend to assume the surface quality of the mold, and if the latter is of high quality, so is the molded part.

Seated on the flange 6 is a mounting member in the form of a counter-flange 8 provided with two elongated holes 10 for the attachment of mounting straps (not shown).

Inside the space 4, but substantially flush with the contact face of flange 6, there is located a relatively, thin metal plate 12, advantageously made of aluminium 12, which is in contact with the tissue investigated, and the temprature of which, rising as an exponential function of time, is used, as already explained, to determine regional blood flow. The temperature of plate 12 is continuously monitored with the aid of a thermocouple, the hot junction 14 of which is embedded in plate 12, and the leads 16, of which are led to the outside via a small hole 18 in the housing 2.

Figure 5:
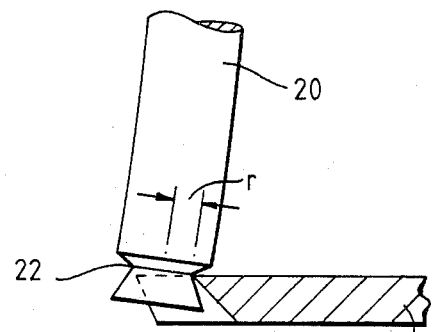

The problem of how to securely hold the plate 12, while reducing its physical contact with the housing or parts thereof to a minimum, has been solved in this preferred embodiment by the provision of three relatively thin, flexing, finger-like rods or prongs 20, located in axial planes of the housing, one end of each of which is fixedly attached to the rear portion of the housing and the other is provided with a notch-like recess or groove 22 (see FIG. 5). The grooves 22 of all of the prongs 20 engage in appropriately shaped and located counternotches 24 of the plate 12. The holding force is provided by the elastic force of the prongs 20 which, to engage the conternotches 24 in the plate 12, must be flexed to slightly spread open.

Figure 4:
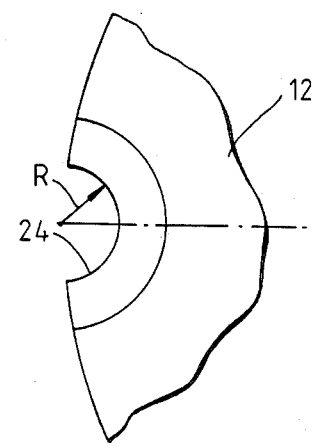

To ensure a contact area that approaches point contact as closely as possible, radius r of the prong notch 22 (see FIG. 5) must be smaller than radius R of the plate counternotch 24 (see FIG. 4).

Although it was stated earlier that the plate 12 was substantially flush with the tissue-contact surface of flange 12, it is quite obvious that while plate 12 should not be sunk below the flange surface (as this would reduce the contact pressure required for good heat transfer), it may advantageously project by about 0.1 mm.

Figure 6:
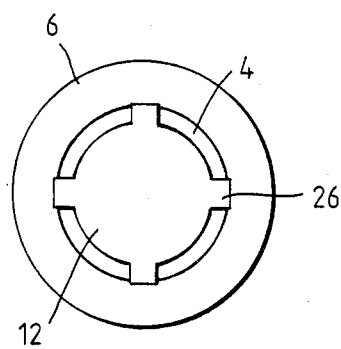
Figure 7:
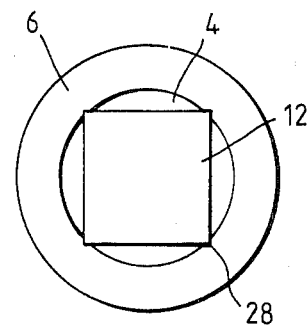

Other mounting methods are illustrated in FIGS. 6 and 7. The plate 12 in FIG. 6 is provided with projections 26, the ends of which are forced into the structural-foam wall of the housing recess. In a similar manner, the four sharp corners 28 of the square plate 12 of FIG. 7 are use for anchoring the plate in the housing.

Figure 8:
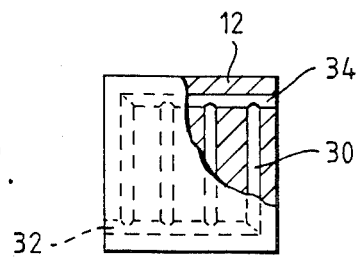

The positive results have been mentioned before of reducing thermal gradients by moderate cooling of the probe plate 12. Such a coolable plate is shown in FIG. 8. It is provided with several interconnected, internal ducts extending in a plane parallel to the surfaces of plate 12, including an inlet opening 32 and an outlet opening 34. Plastic tubing is inserted into these openings, one tube being connected to an air pump, the other to the atmosphere. When the pump is switched on, air at room temperature is drawn through the ducts 30, resulting, within two to three minutes in a drop of plate temperature of 4°-7° C. The inlet air can be cooled below room temperature by introducing a drop of a volatile liquid into the inlet tube. Tests have shown cooling of plate 12—and the adjacent tissue—to result in reduced thermal gradients and, thus, in a shorter measurement time, as already explained.

While the preferred embodiment with its three-prong mounting and its hand, smooth structural foam housing is suitable for most applications, some special clinical applications, such as the monitoring of pressure sores, or the assessment of low-back pain require probes that are both relatively soft and flat. Styrofoam would be a suitable material for such uses, and the problem of its rough, uneven surface can be overcome by convering the entire contact surface (including that of the metal plate 12) with a smooth polyethylene or teflon film. If this film is thin enough, heat transfer from tissue to metal plate will not be impaired to any appreciable degree.

Figure 9:
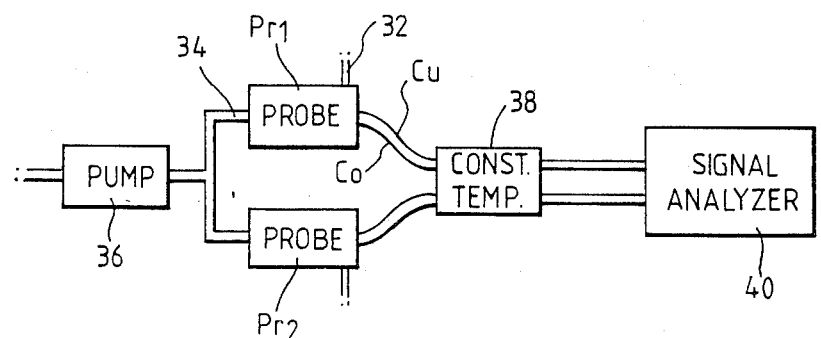

The method and probe according to the invention are eminently suitable for automatic monitoring. FIG. 9 shows the general setup of the device, in which two probes are connected to the analyzer.

There are seen two probes, $Pr_1$ and $Pr_2$, each mounted on a different tissue location, and connected in parallel to an air pump 36. The copper-constantan leads 16 of the respective thermocouples are led into a constant-temperature box 38 which houses the cold junction, and thence into the signal analyzer 40.

Figure 10:
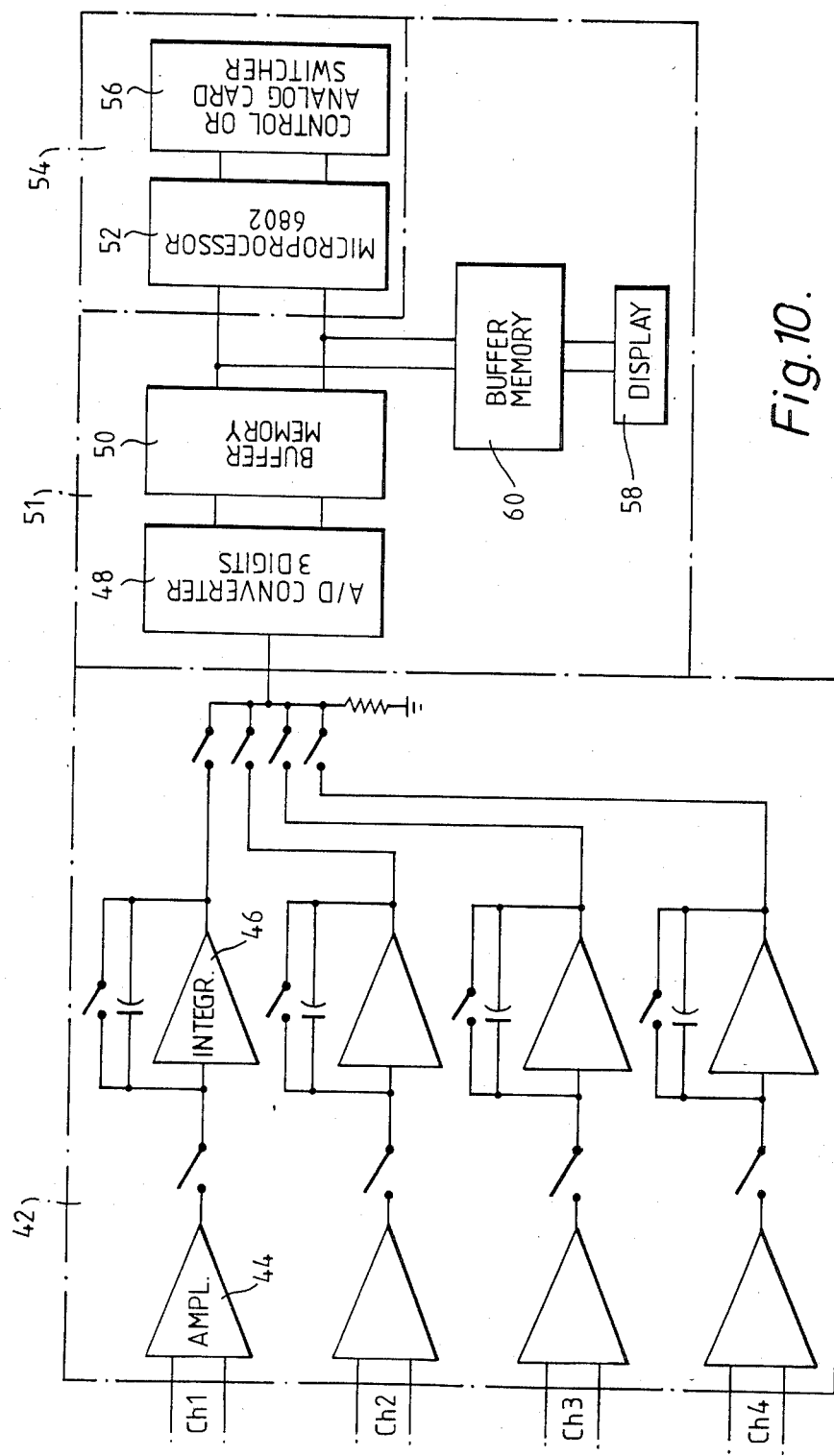

A block diagram of the analyzer 40 is represented in FIG. 10. This particular analyzer has four channels, i.e., it can be used for the simultaneous monitoring of four probes, for instance, for comparing the regional blood flow at two sites on each foot.

There is seen an analog card 42 which, for each of the four channels, comprises an amplifier 44 for the weak thermocouple signals, and an integrating module 46, in which the amplified signals are integrated. The average temperature values for each channel are stored in the buffer memory 50 of a microprocessor 52 on a microprocessor card 54.

The signals processed on the analog card 42 are fed to a three-digit A/D converter 48 on the display card 51, where they are stored in the above-mentioned buffer memory 50. In a typical run, the amplified signals are integrated and averaged for 25 sec, and then digitized and stored for a further 5 sec. This sequence is repeated, say, 64 times.

Each channel is separately addressable by the analog card switcher 56 asscoated with the microprocessor 52.

At the end of each sequence (see above) the arbitrarily selected instants $t_1$ and $t_2$ are introduced into the microprocessor 52, which then proceeds to calculate F according to the expression referred to earlier. Results for each channel are displayed on demand on the display unit 58 via another buffer memory 60, and may also be recorded.

It will be evident to those skilled in the art that the invention is not limited to the details of the foregoing illustrative embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A probe for regional blood flow measurement, comprising:
   a housing of low thermal conduction and heat capacity, at least one face of which is adapted to make contact with a tissue region investigated, said face being provided with a recessed portion;
   a single relatively thin plate made of a material of high thermal conductivity, located in said recessed portion and being substantially flush with said tissue-contacting face of said housing;
   a temperature-sensing means in thermal contact with said plate and adapted to transfer temperature-related information to the outside of said housing, wherein the respective configurations of said plate and said housing are such as to minimize the area of contact between them relative to the area of contact between said plate and said tissue region, in order to minimize heat flow between said plate and said housing.

2. The probe as claimed in claim 1, wherein said housing is made of a structural foam.

3. The probe as claimed in claim 1, wherein said housing is made of styrofoam.

4. The probe as claimed in claim 1, wherein said plate is made of metal.

5. The probe as claimed in claim 1, wherein said temperature-sensing means is a thermocouple, the hot junction of which is in thermal contact with said plate.

6. The probe as claimed in claim 1, further comprising a flange integral with said housing and located at the end of the recessed portion thereof.

7. The probe as claimed in claim 1 wherein said plate is retained in said flush position inside said recessed portion with the aid of a plurality of relatively thin, flexing, finger-like plastic rods located in axial planes of said housing, one end of each of which rods is fixedly attached to a rear portion of said housing, and the other end of each of which rods adjacent to a face portion of said housing is provided with a notch-like recess, each notch-like recess engaging one of a plurality of counter-notches provided at the periphery of said plate, said notches and said counternotches constituting the only points of contact with said plate.

8. The probe as claimed in claim 1, wherein said plate is retained in said housing by means of a plurality of projections, integral with said plate, which projections are forcibly introduced into wall portions of said recess.

9. The probe as claimed in claim 1, wherein said plate comprises a plurality of interconnected internal ducts extending in a plane substantially parallel to the surface of said plate and having an inlet and an outlet opening.

10. A method for carrying our regional blood flow measurements, comprising the steps of:
    providing a minimal-heat-leak probe having a single heat-sensitive face capable of producing signals indicative of the temperature of said face;
    attaching said probe to a tissue region to be investigated, so that signals produced by said heat-sensitive face will be indicative of the temperature of said tissue region;
    exposing said probe to the heat emanating from said tissue region for at least two equal periods of time, a first period $P_1$ starting at a time $t_1$ and ending at a time $t_2$, and a second period $P_2$ starting at a time $t_3$ and ending at a time $t_4$, thereby obtaining a temperature $T_1$ at time $t_1$, a temperature $T_2$ at time $t_2$, a temperature $T_3$ at time $t_3$, and a temperature $T_4$ at time $t_4$;
    using the values thus obtained to determine a temperature-vs.-time curve,
    and applying the expression $$F = \frac{(T_2 - T_1) - (T_4 - T_3)}{I_{34} - I_{12}}$$

to calculate the regional blood flow,
where $I_{12}$ and $I_{34}$ are the areas under said curve that represent the integrals of the temperature over said periods $P_1$ and $P_2$, respectively,
and wherein the highest temperature to be attained by said heat-sensitive face of said probe is lower than local arterial temperature.

11. The method of claim 10 wherein $t_3 = t_2$ and $T_3 = T_2$.

12. The method as claimed in claim 10, wherein all of said temperatures are temperatures averaged over periods of time of between 1 sec and 2 min.

* * * * *